(12) United States Patent
Jin

(10) Patent No.: US 10,391,329 B2
(45) Date of Patent: Aug. 27, 2019

(54) METHODS FOR IMPROVING NEURAL COMMUNICATION BETWEEN TISSUE REGIONS

(71) Applicant: Kosivana Holdings Limited, Limassol (CY)

(72) Inventor: Yi Jin, Irvine, CA (US)

(73) Assignee: KOSIVANA HOLDINGS LIMITED, Limassol (CY)

( * ) Notice: Subject to any disclaimer, the term of this patent is extended or adjusted under 35 U.S.C. 154(b) by 226 days.

(21) Appl. No.: 15/226,578

(22) Filed: Aug. 2, 2016

(65) Prior Publication Data
US 2018/0036550 A1    Feb. 8, 2018

(51) Int. Cl.
| | |
|---|---|
| *A61N 2/00* | (2006.01) |
| *A61N 1/32* | (2006.01) |
| *A61N 1/36* | (2006.01) |
| *A61N 2/02* | (2006.01) |
| *A61N 2/12* | (2006.01) |
| *A61N 1/40* | (2006.01) |

(52) U.S. Cl.
CPC .............. *A61N 2/006* (2013.01); *A61N 1/326* (2013.01); *A61N 1/36014* (2013.01); *A61N 1/36042* (2013.01); *A61N 1/40* (2013.01); *A61N 2/02* (2013.01); *A61N 2/12* (2013.01); *A61N 1/36034* (2017.08)

(58) Field of Classification Search
CPC .......... A61N 1/326; A61N 2/006; A61N 2/02; A61N 2/12
See application file for complete search history.

(56) References Cited

U.S. PATENT DOCUMENTS

2003/0158585 A1* 8/2003 Burnett .............. A61N 1/36021 607/2
2009/0082613 A1* 3/2009 Dennis .................... A61N 2/02 600/13

* cited by examiner

*Primary Examiner* — Christine H Matthews
(74) *Attorney, Agent, or Firm* — Saliwanchik, Lloyd & Eisenschenk

(57) ABSTRACT

Described are methods for the improvement of neural communication between implanted and existing tissue. Methods herein use synchronous low frequency magnetic or electric stimulation of both regions to enhance communication and facilitate regeneration of nerve fibers across the tissue interface.

19 Claims, 3 Drawing Sheets

METHODS FOR IMPROVING NEURAL COMMUNICATION BETWEEN TISSUE REGIONS

BACKGROUND OF THE INVENTION

Tissue implantation or grafting is a common surgical procedure in which tissue is transplanted from one area to another on a person's body, or from another person, without bringing its own blood supply. This is in contrast to flap surgery, in which the grafted tissue has an intact blood supply. The implanted tissue may be engineered, such as from stem cells and a collagenous scaffold. One important type of tissue engineering involves the formation of neural tissue, which is implanted to promote nerve regeneration and to repair damaged nerves. It is also possible to create implanted tissue via intravenous stem cell injections, through natural concentration of stem cells in affected regions.

Neural communication is required between the implanted tissue and existing tissue in order to allow sensory and functional information to be passed between the host tissue and implanted tissue. The implanted tissue generally contains nerve fibers that provide sensory or functional communication between the implanted tissue and the host. In many cases following the implantation procedure, however, neural communication between the implanted tissue and the existing tissue is limited or nonexistent, even though the implanted tissue is viable with a reasonable blood supply.

Currently, procedures used to improve neural communication with implanted tissue include peripheral nerve reconstruction, in which nerves are cut and re-approximated using very small sutures. Another option is bio-artificial nerve guidance conduits in order to guide axonal regrowth and connectivity. However, surgical procedures such as these are time consuming, highly invasive, and involve a long recovery period for the patient. It is apparent that a non-invasive approach would have significant benefits over existing technology.

SUMMARY

Magnetic stimulation utilizes a pulsed magnetic field applied to a region near a target area. The magnetic pulses affect neuronal firing in the target area, either directly through active depolarization with a high power magnetic field, or indirectly through entrainment and field effect with a low power magnetic field. It has been shown that low frequency (<30 Hz) magnetic pulses enhance communication through nerves in the target area. A magnetic field generates an induced electric field in the neurons and surrounding tissue. The electric field from the magnetic pulses has an entrainment effect on neurons in the area, encouraging synchronous firing between nearby neurons.

By providing synchronous magnetic pulses to implanted tissue and existing tissue, it is possible to improve communication between the two, resulting in better passing of sensory information and functional control between the brain and implanted tissue. In addition, synchronous stimulation encourages the regeneration of nerve fibers across the interface between the two regions of tissue. Improved communication can occur via, for example, improved communication between existing nerves, by growth of new nerves, and/or via regeneration of nerves, including axonal growth into nerve grafts and/or into the distal end of severed nerves.

In one aspect, the subject invention provides methods of improving neural communication through the interface between a first distinct region of tissue and a second distinct region of tissue in the body of a person, wherein the method comprises administering repetitive magnetic field pulses synchronously to both regions of tissue.

Due to the spreading of the magnetic field, it may be that a single magnetic field source affects both implanted and existing tissue. However, two or more separate magnetic field sources may be used to ensure implanted and existing tissue are properly targeted.

Thus, in some embodiments of at least one aspect described above, the magnetic pulses administered to the first region of tissue and the second region of tissue are generated by a single magnetic field source. In some embodiments of at least one aspect described above, the magnetic pulses administered to the first region of tissue and the second region of tissue are generated by more than one magnetic field source.

Preferably the magnetic pulses are generated using an electromagnet, but other methods may also be used. In some embodiments of at least one aspect described above, the magnetic pulses are generated by a coil or a moving permanent magnet.

When low frequency magnetic pulses are applied, neural communication within tissue and between tissues is improved. Preferably, the frequency of magnetic pulses is fixed at or near a target frequency, but it may also vary within a range, which may result in improved efficacy. In some embodiments of at least one aspect described above, the magnetic pulse frequency is fixed at or near a target frequency. In some embodiments of at least one aspect described above, the magnetic pulse frequency hops periodically about an average target frequency. This hopping may be random or may be in a fixed pattern. In some embodiments of at least one aspect described above, the magnetic pulse frequency hops periodically between random values within a range about the average target frequency. In some embodiments of at least one aspect described above, the magnetic pulse frequency hops periodically in a specific pattern about the average target frequency.

The frequency of magnetic pulses should be low in order to improve neural communication. In some embodiments of at least one aspect described above, the magnetic pulse target frequency is from about 1 Hz to about 10 Hz. In some embodiments of at least one aspect described above, the magnetic pulse target frequency is from about 10 Hz to about 30 Hz.

Because much of the method of action for improved communication can be achieved through entrainment, it is not necessary that stimulation be super-threshold, able to actively depolarize neurons. Instead, the magnetic field strength can be set over a wide range. In some embodiments of at least one aspect described above, the strength of the magnetic pulses is from about 10 Gauss to about 4 Tesla. In general, however, the effect may be improved if the strength of the magnetic field at the target location is strengthened, up to the point where stimulation is bothersome or painful to the patient. In some embodiments of at least one aspect described above, the strength of the magnetic pulses is adjusted based on the tolerance of the patient.

Magnetic pulses induce an electric current or electric voltage potential in or near nerves in the implanted tissue and existing tissue. Therefore, in addition to magnetic stimulation, it is also possible to achieve similar benefits through direct electrical stimulation, either transcutaneously with electrodes placed on the skin above the target region, or subcutaneously, using, for example, needle-electrodes, or an implanted electrode array. In one aspect are methods of improving neural communication between a first region of tissue and a second region of tissue in the body of a person comprising administering alternating electric currents synchronously to both regions of tissue.

The synchronous alternating electric currents in the two regions may be generated by a single source, where electric current flows through the interface between the two regions, or by multiple sources, where each region contains its own electric current source. In some embodiments of at least one aspect described above, the electric currents administered to the first region of tissue and the second region of tissue are generated by a single electric current source where the current travels across the interface between the regions. In some embodiments of at least one aspect described above, the electric currents administered to the first region of tissue and the second region of tissue are generated by more than one electric current source that stimulates the two regions concurrently.

When low frequency electric currents are applied to regions of tissue, neural communication within a tissue and between tissues is improved. Preferably, the frequency of electric currents is fixed at or near a target frequency, but it may also vary within a range, which may result in improved efficacy. In some embodiments of at least one aspect described above, the electric current frequency is fixed at or near a target frequency. In some embodiments of at least one aspect described above, the electric current frequency hops periodically about an average target frequency. This hopping may be random or may be in a fixed pattern. In some embodiments of at least one aspect described above, the electric current frequency hops periodically between random values within a range about the average target frequency. In some embodiments of at least one aspect described above, the electric frequency hops periodically in a specific pattern about the average target frequency.

The frequency of electric current should be low in order to improve neural communication. In some embodiments of at least one aspect described above, the electric current target frequency is from about 1 Hz to about 10 Hz. In some embodiments of at least one aspect described above, the electric current target frequency is from about 10 Hz to about 30 Hz.

The regions of tissue may be endogenous or engineered. For example, in tissue grafting or in a tissue flap, both regions may be endogenous. Engineered tissue may be generated using stem cells or another technique, or may be transplanted from another region of the body or from a donor. Engineered tissue may also result from stem cell injections, either directly to the treatment site or intravenously, or by stem cell implantation. In some embodiments of at least one aspect described above, the first region of tissue is engineered and the second region of tissue is endogenous. In some embodiments of at least one aspect described above, the first region of tissue is transplanted and the second region of tissue is endogenous. In some embodiments of at least one aspect described above, the first region of tissue is generated from stem cell injections and the second region of tissue is endogenous.

The type of tissue may vary because tissue implantation can be used to improve functionality in a variety of organs in the body. In some embodiments of at least one aspect described above, the first or second region of tissue comprises muscle tissue. In some embodiments of at least one aspect described above, the first or second region of tissue comprises brain tissue. In some embodiments of at least one aspect described above, the first or second region of tissue comprises skin tissue. Other embodiments include nerve tissue including (nerve grafts), pancreas, gastrointestinal, kidney, urogenital, and bone tissue.

BRIEF DESCRIPTION OF THE DRAWINGS

A better understanding of the features and advantages of the systems and methods provided will be obtained by reference to the following detailed description that sets forth illustrative embodiments and the accompanying drawings of which.

DETAILED DESCRIPTION

Figure 1:
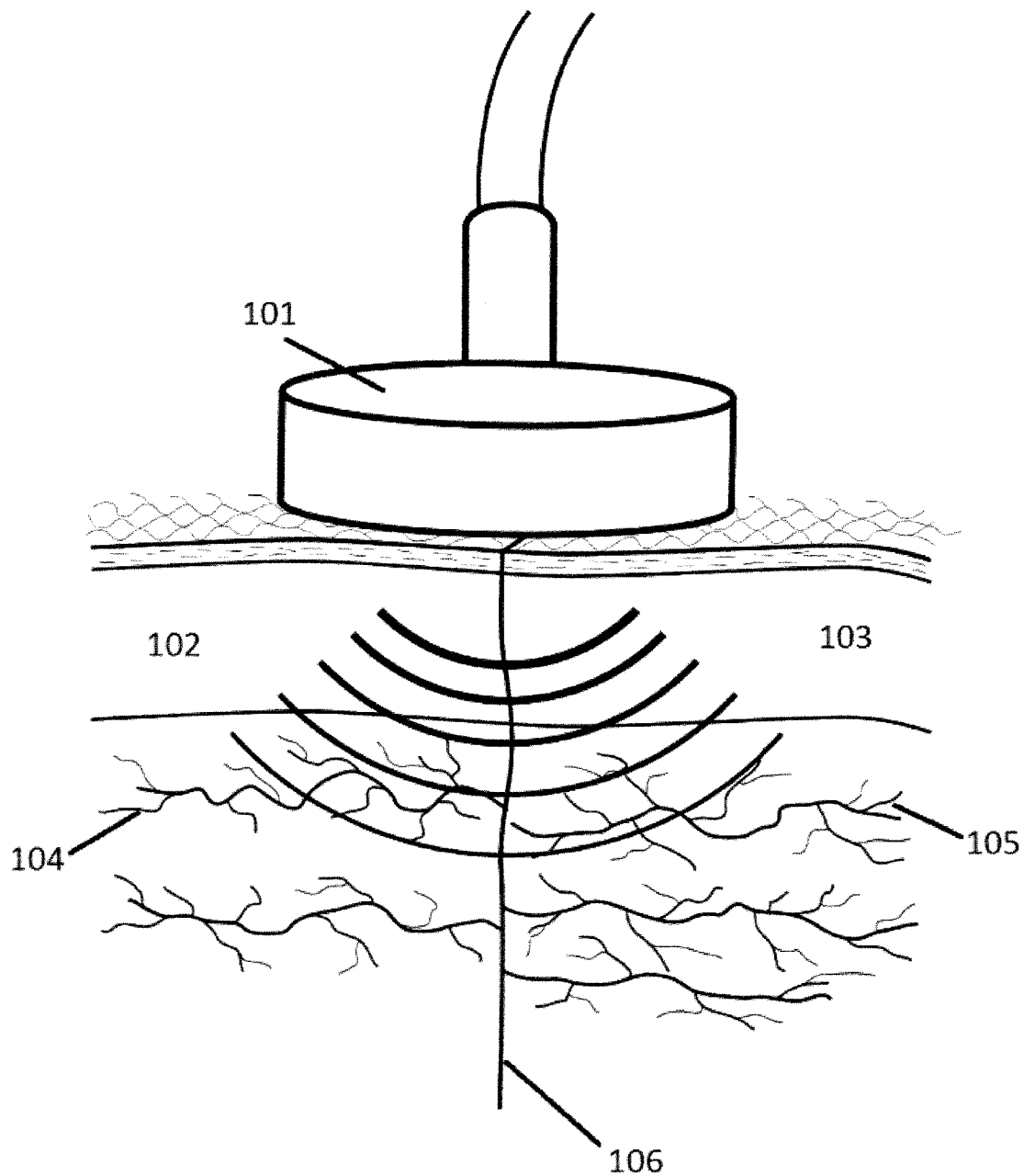
FIG. 1 shows an exemplary method in which a magnetic field is generated using a single coil, where the magnetic field provides synchronous magnetic stimulation to two distinct regions of tissue.

While certain embodiments have been provided and described herein, it will be readily apparent to those skilled in the art that such embodiments are provided by way of example only. It should be understood that various alternatives to the embodiments described herein may be employed, and are part of the invention described herein.

Described herein are methods for novel, effective improvement of neural communication between two distinct regions of tissue. In some embodiments, described are methods that use repetitive magnetic stimulation (rMS) to stimulate the two regions synchronously, which improves communication and may facilitate nerve regeneration in the targeted region. It has been shown that low frequency magnetic field stimulation enhances communication of nerves in a single targeted region; however, it is also possible to apply synchronous magnetic stimulation to two distinct regions of tissue to improve communication between the two regions.

Improved communication can occur via, for example, improved communication between existing nerves, by growth of new nerves, and/or via regeneration of nerves, including axonal growth into nerve grafts and/or into the distal end of severed nerves.

The term "target region," when referring to rMS treatment, is a region where magnetic stimulation is applied, and may encompass one or two regions of tissue.

The term "region of tissue," when referring to rMS treatment, is a region of tissue with a boundary between it and another region of tissue. The tissue may be endogenous, already existing in the body, engineered, such as with stem cells, or transplanted, either from a different region of the body or from a donor.

Described herein are methods that improve neural communication through the interface between two distinct regions of tissue using synchronous low frequency stimulation to both regions. These methods involve no medication, although medication may be administered in conjunction with the treatment without necessarily altering the effects of the treatment.

Implanted tissue is often used to repair and improve the function of existing damaged tissue. Implanted tissue may be endogenous, engineered, or donated. Tissue may also form through the concentration of injected stem cells. Often, implanted tissue contains nerve cells that are intended to provide sensory or functional information to or from the implanted tissue. It may be the case that the implanted tissue does not have effective neural communication with adjacent existing tissue through the interface between the two, even though the implanted tissue is viable through the existing blood supply.

When a signal is transmitted through a nerve fiber, a minimum transit time is generally required, which is about 50 milliseconds. This means that the highest frequency at which the nerve can fire is about 20 Hz (20 times per second). Magnetic pulses or alternating electric current administered to a target location on the nerve cause a voltage potential in the nerve fibers, and if the magnetic pulses or electric current have a low frequency (less than 30 Hz), then communication in the nerve fiber becomes enhanced. It has been shown that low frequency stimulation, either electrically or with pulsed magnetic fields, improves neural communication in undamaged tissue. However, in accordance with the subject invention it is also the case that low frequency electrical or magnetic stimulation also improves communication across the boundary between two distinct tissue regions, such as between implanted tissue and existing tissue, when the stimulation is provided synchronously to both tissues on either side of the boundary. If the implanted tissue is formed using stem cells, synchronous low frequency stimulation allows for the formation of nerve fibers across the tissue boundary.

In one aspect are methods of improving neural communication through the interface between a first distinct region of tissue and a second distinct region of tissue in the body of a subject comprising administering repetitive magnetic field pulses synchronously to both regions of tissue. Due to the spreading of the magnetic field, it may be that a single magnetic field source affects both the implanted and existing tissue; however, two or more separate magnetic field sources may be used to ensure implanted and existing tissue is properly targeted. In some embodiments of at least one aspect of the subject invention, the magnetic pulses administered to the first region of tissue and the second region of tissue are generated by a single magnetic field source. In some embodiments of at least one aspect of the subject invention, the magnetic pulses administered to the first region of tissue and the second region of tissue are generated by more than one magnetic field source.

Preferably the magnetic pulses are generated using an electromagnet, but other methods may also be used. In some embodiments of at least one aspect described above, the magnetic pulses are generated by a coil or a moving permanent magnet.

When magnetic pulses are applied that are low frequency, neural communication within tissue and between tissues is improved. Preferably, the frequency of magnetic pulses is fixed at or near a target frequency, but it may also vary within a range, which may result in improved efficacy. In some embodiments of at least one aspect described above, the magnetic pulse frequency is fixed at or near a target frequency. In some embodiments of at least one aspect described above, the magnetic pulse frequency hops periodically about an average target frequency. This hopping may be random or may be in a fixed pattern. In some embodiments of at least one aspect described above, the magnetic pulse frequency hops periodically between random values within a range about the average target frequency. In some embodiments of at least one aspect described above, the magnetic pulse frequency hops periodically in a specific pattern about the average target frequency.

The frequency of magnetic pulses should be low in order to improve neural communication. In some embodiments of at least one aspect described above, the magnetic pulse target frequency is from about 1 Hz to about 10 Hz. In some embodiments of at least one aspect described above, the magnetic pulse target frequency is from about 10 Hz to about 30 Hz.

Because much of the method of action for improved communication can be achieved through entrainment, it is not necessary that stimulation be super-threshold, able to actively depolarize neurons. Instead, the magnetic field strength can be set over a wide range. In some embodiments of at least one aspect described above, the strength of the magnetic pulses is from about 10 Gauss to about 4 Tesla. In general, however, the effect may be improved if the strength of the magnetic field at the target location is strengthened, up to the point where stimulation is bothersome or painful to the patient. In some embodiments of at least one aspect described above, the strength of the magnetic pulses is adjusted based on the tolerance of the patient.

Magnetic pulses induce an electric current or electric voltage potential in or near nerves in the implanted tissue and existing tissue. Therefore, in addition to magnetic stimulation, it is also possible to achieve similar benefits through direct electrical stimulation, either transcutaneously with electrodes placed on the skin above the target region, or subcutaneously, possibly using needle-electrodes. or an implanted electrode array. In one aspect are methods of improving neural communication between a first region of tissue and a second region of tissue in the body of a person comprising administering repetitive electrical current pulses synchronously to both regions of tissue.

The synchronous alternating electric currents in the two regions may be generated by a single source, where electric current flows through the interface between the two regions, or by multiple sources, where each region contains its own electric current source. In some embodiments of at least one aspect described above, the electric currents administered to the first region of tissue and the second region of tissue are generated by a single electric current source, where current flows through the interface between the regions. In some embodiments of at least one aspect described above, the electric currents administered to the first region of tissue and the second region of tissue are generated by more than one electric current source that stimulates the two regions concurrently.

When low frequency electric currents are applied to regions of tissue, neural communication within tissue and between tissues is improved. Preferably, the frequency of electric currents is fixed at or near a target frequency, but it may also vary within a range, which may result in improved efficacy. In some embodiments of at least one aspect described above, the electric current frequency is fixed at or near a target frequency. In some embodiments of at least one aspect described above, the electric current frequency hops periodically about an average target frequency. This hopping may be random or may be in a fixed pattern. In some embodiments of at least one aspect described above, the electric current frequency hops periodically between random values within a range about the average target frequency. In some embodiments of at least one aspect described above, the electric frequency hops periodically in a specific pattern about the average target frequency.

The frequency of electric current should be low in order to improve neural communication. In some embodiments of at least one aspect described above, the electric current target frequency is from about 1 Hz to about 10 Hz. In some embodiments of at least one aspect described above, the electric current target frequency is from about 10 Hz to about 30 Hz. The regions of tissue may be endogenous or engineered. For example, in tissue grafting or in a tissue flap, both regions may be endogenous. Engineered tissue may be generated using stem cells or another technique, or may be transplanted from another region of the body or from a donor. Engineered tissue may also result from stem cell injections or stem cell implantation. In some embodiments of at least one aspect described above, the first region of tissue is engineered and the second region of tissue is endogenous. In some embodiments of at least one aspect described above, the first region of tissue is transplanted and the second region of tissue is endogenous. In some embodiments of at least one aspect described above, the first region of tissue is generated from stem cell injections and the second region of tissue is endogenous.

The type of tissue may vary because tissue implantation can be used to improve functionality in a variety of organs in the body. In some embodiments of at least one aspect described above, the first or second region of tissue comprises muscle tissue. In some embodiments of at least one aspect described above, the first or second region of tissue comprises brain tissue. In some embodiments of at least one aspect described above, the first or second region of tissue comprises skin tissue. Other embodiments include nerve tissue (including nerve grafts), pancreas, gastrointestinal, kidney, urogenital, and bone tissue.

FIG. 1 shows an exemplary method in which a synchronous low frequency pulsed magnetic field is generated by a coil (101), which is placed near the interface (106) of two distinct regions of tissue (102, 103). The nerve fibers in the two tissue regions (104, 105) are not directly connected across the interface, but the synchronous magnetic field facilitates communication between the disconnected fibers, and the potential regeneration of new nerve fibers across the interface.

Figure 2:
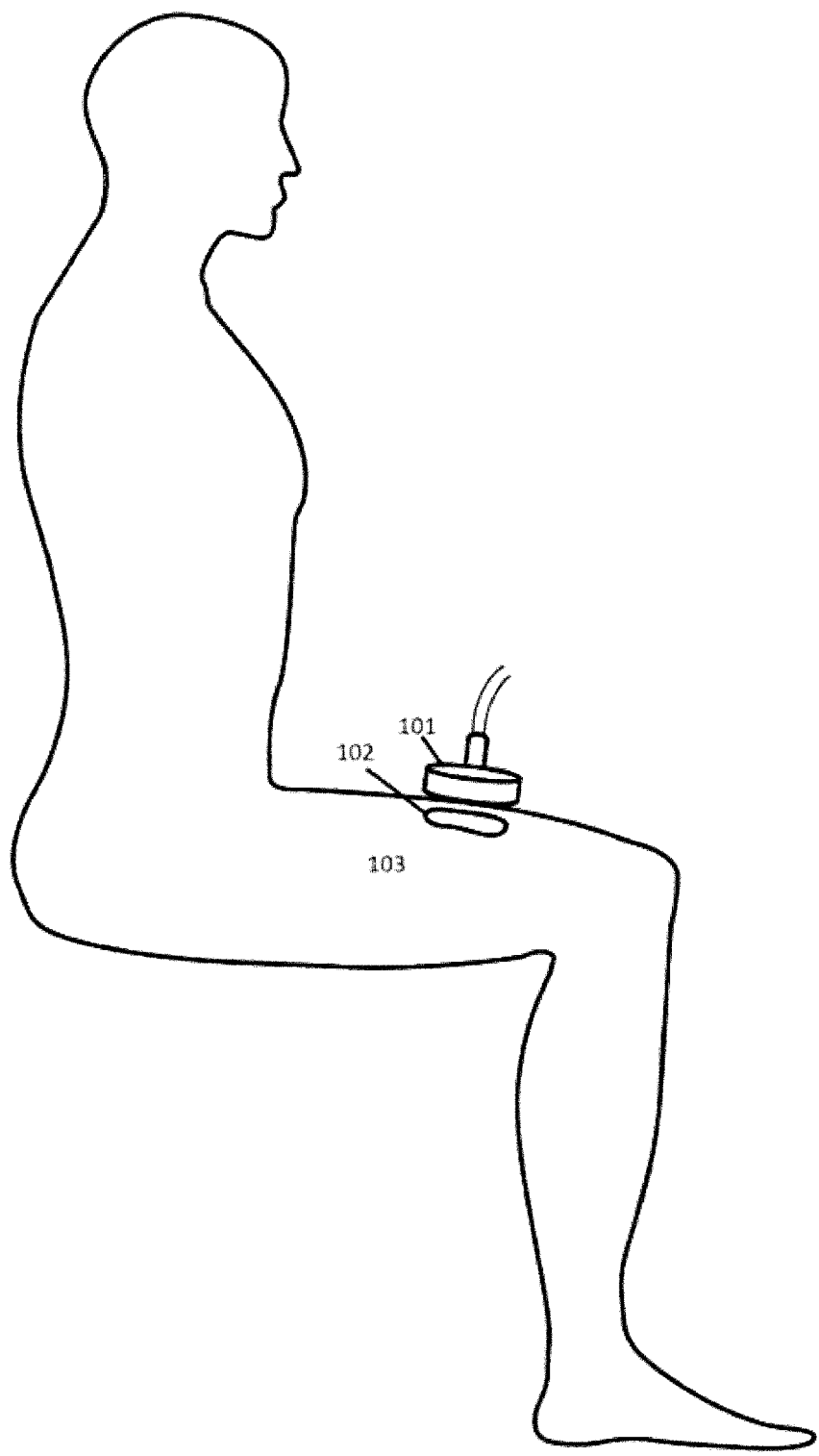
FIG. 2 shows an exemplary method in which a single coil is placed over a region of implanted tissue, so that the synchronous magnetic field extends to both the implanted tissue and the existing tissue.

FIG. 2 shows an exemplary method in which a coil (101) generates a magnetic field above a region of implanted tissue (102). The magnetic field extends to affect both the implanted tissue and existing tissue (103) in the target region.

Figure 3:
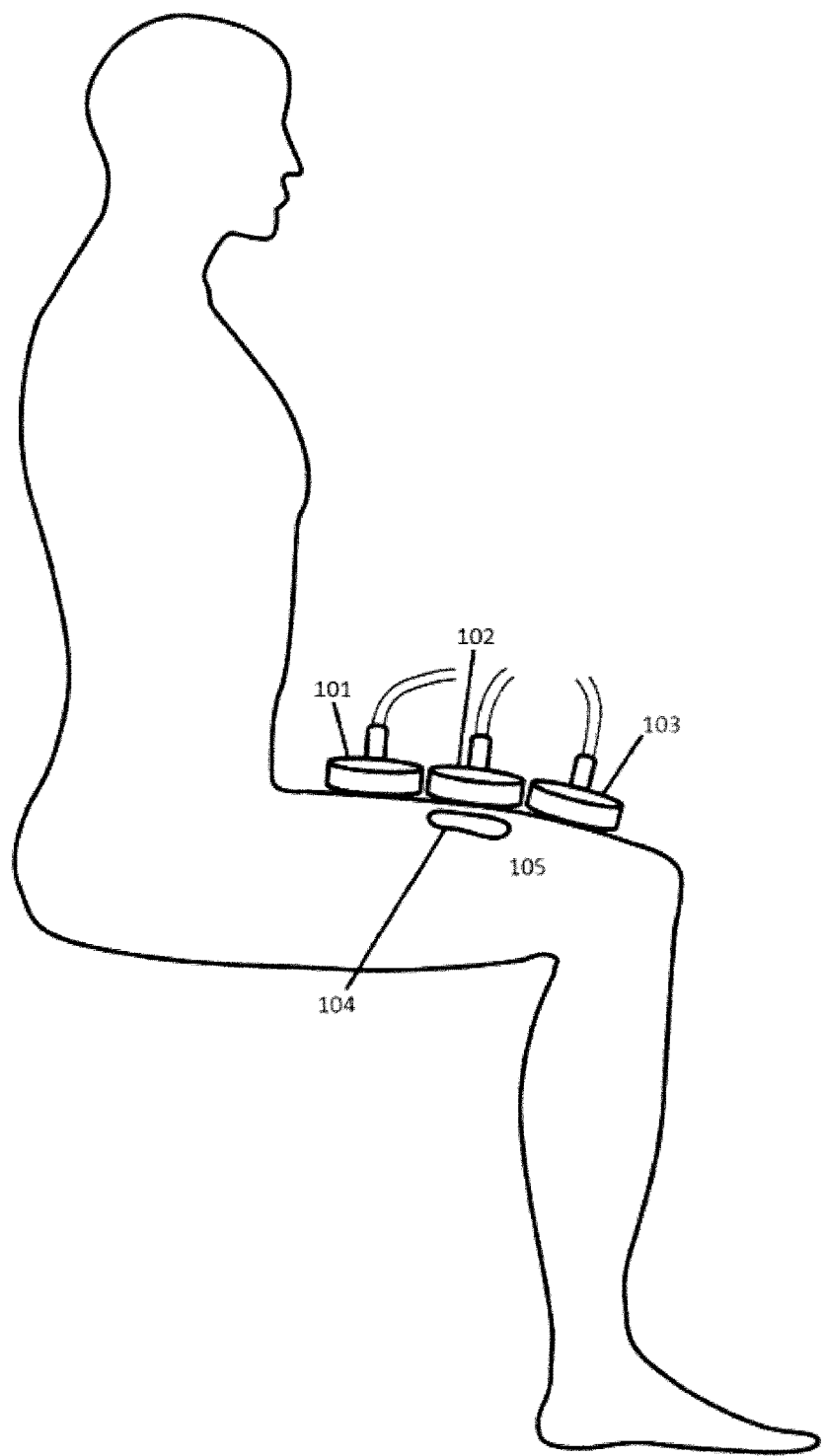
FIG. 3 shows an exemplary method in which three coils are placed so that they synchronously stimulate a region of implanted tissue as well as the existing tissue on either side.

FIG. 3 shows an exemplary method in which multiple coils are used to provide synchronous magnetic stimulation to implanted and existing tissue. In this method, a central coil (102) is placed so that the highest energy magnetic field possible is delivered to the implanted tissue (104), while the two side coils (101, 103) are placed to deliver the highest energy magnetic field possible to the region of existing tissue (105) surrounding the implanted tissue.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above descriptions of illustrated embodiments of the system, methods, or devices are not intended to be exhaustive or to be limited to the precise form disclosed. While specific embodiments of, and examples for, the system, methods, or devices are described herein for illustrative purposes, various equivalent modifications are possible within the scope of the system, methods, or devices, as those skilled in the relevant art will recognize. The teachings of the system, methods, or devices provided herein can be applied to other processing systems, methods, or devices, not only for the systems, methods, or devices described.

The elements and acts of the various embodiments described can be combined to provide further embodiments. These and other changes can be made to the system in light of the above detailed description.

In general, in the following claims, the terms used should not be construed to limit the system, methods, or devices to the specific embodiments disclosed in the specification and the claims, but should be construed to include all processing systems that operate under the claims. Accordingly, the system, methods, and devices are not limited by the disclosure, but instead the scopes of the system, methods, or devices are to be determined entirely by the claims.

While certain aspects of the system, methods, or devices are presented below in certain claim forms, the inventor contemplates the various aspects of the system, methods, or devices in any number of claim forms. Accordingly, the inventors reserve the right to add additional claims after filing the application to pursue such additional claim foul's for other aspects of the system, methods, or devices.

EMBODIMENTS

Specific embodiments of the invention include the following:

1. A method of improving neural communication through the interface between a first distinct region of tissue and a second distinct region of tissue in the body of a person comprising administering repetitive magnetic field pulses synchronously to both regions of tissue.
2. The method of Embodiment 1 wherein the magnetic pulses administered to the first region of tissue and the second region of tissue are generated by a single magnetic field source.
3. The method of Embodiment 1 wherein the magnetic pulses administered to the first region of tissue and the second region of tissue are generated by more than one magnetic field source.
4. The method of Embodiment 1 wherein the magnetic pulses are generated by a coil or a moving permanent magnet.
5. The method of Embodiment 1 wherein the magnetic pulse frequency is fixed at or near a target frequency.
6. The method of Embodiment 1 wherein the magnetic pulse frequency hops periodically about an average target frequency.
7. The method of Embodiment 5 or 6 wherein the magnetic pulse target frequency is from about 1 Hz to about 10 Hz.
8. The method of Embodiment 5 or 6 wherein the magnetic pulse target frequency is from about 10 Hz to about 30 Hz.
9. The method of Embodiment 1 wherein the strength of the magnetic pulses is from about 10 Gauss to about 4 Tesla.
10. The method of Embodiment 1 wherein the strength of the magnetic pulses is adjusted based on the tolerance of the patient.

11. A method of improving neural communication between a first region of tissue and a second region of tissue in the body of a person comprising administering alternating electric currents synchronously to both regions of tissue.

12. The method of Embodiment 11 wherein the electric currents administered to the first region of tissue and the second region of tissue are generated by a single electric current source, where electric current flows through the interface between the regions.

13. The method of Embodiment 11 wherein the electric currents administered to the first region of tissue and the second region of tissue are generated by more than one electric current source that stimulates the two regions concurrently.

14. The method of Embodiment 11 wherein the electric current frequency is fixed at or near a target frequency.

15. The method of Embodiment 11 wherein the electric current frequency hops periodically about an average target frequency.

16. The method of Embodiment 14 or 15 wherein the electric current target frequency is from about 1 Hz to about 10 Hz.

17. The method of Embodiment 14 or 15 wherein the electric current target frequency is from about 10 Hz to about 30 Hz.

18. The method of Embodiment 1 or 11 wherein the first region of tissue is engineered and the second region of tissue is endogenous.

19. The method of Embodiment 1 or 11 wherein the first region of tissue is transplanted and the second region of tissue is endogenous.

20. The method of Embodiment 1 or 11 wherein the first region of tissue is generated from stem cell injections and the second region of tissue is endogenous.

21. The method of Embodiment 1 or 11 wherein the first or second region of tissue comprises muscle tissue.

22. The method of Embodiment 1 or 11 wherein the first or second region of tissue comprises brain tissue.

23. The method of Embodiment 1 or 11 wherein the first or second region of tissue comprises skin tissue.

While embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

The invention is described in greater detail by the following non-limiting examples.

Example 1

An 87-year-old female patient with moderate Alzheimer's disease, presented with a Mini-Mental State Examination (MMSE) score of 0, with severe deficits in memory, cognition, speech aphasia, and motor catatonia. The patient was administered stem cells via IV one year prior to therapy, with no improvement in symptoms. Experts believed that stem cells had entered regions of the brain and were viable, but communication had not been established.

Transcranial magnetic pulses were administered over the frontal lobe at approximately 10 Hz, placed so that pulses would synchronously stimulate both the stem cell tissue and existing tissue. 6 second pulse trains were used, with 54 second inter-train interval for 30 trains.

Communication between implanted stem cell tissue and existing tissue was greatly improved, based on EEG data. Following 2 weeks of stimulation, her MMSE score increased to 5, catatonia was reduced by 30%, and the patient began speaking in full sentences.

Example 2

An 8-year-old male patient had left side cerebrovascular injury due to a traffic accident. The patient had normal developmental history, but after the accident, he presented with speech aphasia, general fine motor loss, loss of function of the left leg, and had slowed cognitive comprehension. The patient had been administered stem cells via IV one month prior to therapy, with no improvement in symptoms. Experts believed that stem cells had entered regions of the brain and were viable, but communication had not been established.

Transcranial magnetic pulses were administered over the left motor cortex and frontal lobe at approximately 10 Hz, placed so that pulses would synchronously stimulate both the stem cell tissue and existing tissue. 8 second pulse trains were used, with 52 second inter-train intervals for 40 trains. After 2 months of therapy, general fine motor function improved by 30%. The patient was capable of sticking out his tongue, began making sounds, recovered facial expressions, and improved cognitive processing speed.

What is claimed is:

1. A method of improving neural communication through an interface between a first distinct region of tissue and a second distinct region of tissue in the body of a person, the method comprising administering repetitive magnetic field pulses synchronously at a magnetic pulse frequency to both regions of tissue, wherein the magnetic pulse frequency changes periodically about an average target frequency that is 30 Hz or less.

2. The method of claim 1 wherein the magnetic pulses administered to the first region of tissue and the second region of tissue are generated by a single magnetic field source.

3. The method of claim 1 wherein the magnetic pulses administered to the first region of tissue and the second region of tissue are generated by more than one magnetic field source.

4. The method of claim 1 wherein the magnetic pulses are generated by a coil or a moving permanent magnet.

5. The method of claim 1 wherein the average target frequency is from about 1 Hz to about 10 Hz.

6. The method of claim 1 wherein the average target frequency is from about 10 Hz to about 30 Hz.

7. The method of claim 1 wherein a strength of the magnetic pulses is from about 10 Gauss to about 4 Tesla.

8. The method of claim 1 wherein a strength of the magnetic pulses is adjusted based on a tolerance of a patient.

9. A method of improving neural communication between a first region of tissue and a second region of tissue in the body of a person, the method comprising administering alternating currents generated by at least one current source synchronously at an electric current frequency to both regions of tissue, wherein the electric current frequency changes periodically about an average target frequency that is 30 Hz or less.

10. The method of claim 9 wherein the at least one current source is a single electric current source, wherein current flows through an interface between the regions.

11. The method of claim 9 wherein the at least one current source is more than one electric current source that stimulates the two regions concurrently.

12. The method of claim 9 wherein the average target frequency is from about 1 Hz to about 10 Hz.

13. The method of claim 9 wherein the average target frequency is from about 10 Hz to about 30 Hz.

14. The method of claim 1 or 9 wherein the first region of tissue is engineered and the second region of tissue is endogenous.

15. The method of claim 1 or 9 wherein the first region of tissue is transplanted and the second region of tissue is endogenous.

16. The method of claim 1 or 9 wherein the first region of tissue is generated from stem cell injections and the second region of tissue is endogenous.

17. The method of claim 1 or 9 wherein the first or second region of tissue comprises muscle tissue.

18. The method of claim 1 or 9 wherein the first or second region of tissue comprises brain tissue.

19. The method of claim 1 or 9 wherein the first or second region of tissue comprises skin tissue.

* * * * *